(12) United States Patent
Hanson et al.

(10) Patent No.: US 12,115,134 B2
(45) Date of Patent: Oct. 15, 2024

(54) COMPOSITIONS AND METHODS FOR TREATING ENDOCRINE DISEASES AND DISORDERS

(71) Applicant: Olfactive Biosolutions, LLC, Mountain View, CA (US)

(72) Inventors: Christopher Hanson, Mountain View, CA (US); William Harries, Boulder Creek, CA (US)

(73) Assignee: Olfactive Biosolutions, LLC, Mountain View, CA (US)

( * ) Notice: Subject to any disclaimer, the term of this patent is extended or adjusted under 35 U.S.C. 154(b) by 0 days.

(21) Appl. No.: 18/430,796

(22) Filed: Feb. 2, 2024

(65) Prior Publication Data
US 2024/0165061 A1    May 23, 2024

Related U.S. Application Data

(60) Provisional application No. 63/615,100, filed on Dec. 27, 2023.

(51) Int. Cl.
| | | |
|---|---|---|
| A61K 31/045 | (2006.01) | |
| A61K 31/085 | (2006.01) | |
| A61K 31/19 | (2006.01) | |
| A61K 31/20 | (2006.01) | |

(52) U.S. Cl.
CPC .......... *A61K 31/045* (2013.01); *A61K 31/085* (2013.01); *A61K 31/19* (2013.01); *A61K 31/20* (2013.01)

(58) Field of Classification Search
CPC ................................ A61K 31/19; A61K 31/20
See application file for complete search history.

*Primary Examiner* — Deborah D Carr
(74) *Attorney, Agent, or Firm* — Francis Law Group (57) ABSTRACT

Disclosed herein are compounds and ligands, and compositions formed therewith, that modulate insulin secretion and suppress appetite by activating ectopic olfactory receptors. Also disclosed herein are methods for using the compositions to treat endocrine diseases, such as type-2 diabetes, and disorders, such as abnormal insulin secretion.

8 Claims, 2 Drawing Sheets

COMPOSITIONS AND METHODS FOR TREATING ENDOCRINE DISEASES AND DISORDERS

CROSS-REFERENCES TO RELATED APPLICATIONS

This application claims the benefit of U.S. Provisional Application No. 63/615,100, filed on Dec. 27, 2023.

FIELD OF THE INVENTION

The present invention relates to compositions and methods for treating endocrine disorders. More particularly, the present invention relates to compositions and methods for treating diabetes mellitus and obesity by modulating ectopic olfactory activity.

BACKGROUND OF THE INVENTION

As is well established, obesity is a disorder that affects the health of millions of adults and youth in the U.S. According to a 2021 Centers for Disease Control and Prevention (CDC) survey, the prevalence of obesity in the U.S. between 2017-2020 was 41.9% in adults (i.e., adults having a body mass index (BMI) of greater than or equal to 30 kg/m², 9.2% of which being severely obese (i.e., adults having a BMI than or equal to 40 kg/m²), and 19.7% in youth.

Based on earlier CDC data, the above-noted prevalence of adult obesity increased approximately 10% over a ten (10) year period, and the prevalence of youth obesity increased approximately 7% during the same period.

The increasing prevalence of obesity is also a growing U.S. national security concern due to difficulties maintaining operational readiness among current servicemembers and shrinking recruitment pools. An October 2023 study by the American Security Project (ASP) reflects that military obesity rates across active duty personal increased by approximately 11.2% between 2012 and 2022, according to an October 2023 study. The study also reflects that 68% of active duty servicemembers are either overweight or obese, and that eating disorders in the military also increased by approximately 79% between 2017 and 2021.

The rapidly increasing prevalence of obesity is not limited to the U.S. Indeed, the increasing prevalence of obesity is generally regarded as an epidemic worldwide.

In addition to a reduced life expectancy compared to non-obese individuals, and the public stigma and discrimination associated with obesity, obese individuals also often present with diabetes mellitus.

Indeed, the International Diabetes Federation (IDF) reported that in 2021 alone over 300 million obese individuals worldwide were afflicted with diabetes mellitus.

Diabetes mellitus is generally characterized by hyperglycemia associated with abnormal insulin secretion, i.e., insufficient insulin production by the pancreas or insulin resistance exhibited by endogenous cells.

As is well established, in most instances, insulin secretion is induced by pancreatic β-cells when glucagon-like peptide-1 (GLP-1) binds to and activates GLP-1 receptor proteins on endogenous gastrointestinal (GI) cells, such as enteroendocrine L-cells.

In addition to inducing insulin secretion, it has been found that GLP-1 also decreases the rate of gastric emptying and acid secretion, resulting in reduced appetite and, thereby, weight loss.

Obese individuals that present with diabetes mellitus; particularly, type-2 diabetes mellitus, are typically difficult to treat due to long term unhealthy eating patterns and a myriad of physiological complexities associated with the mechanisms of appetite control and energy metabolism. Treatment of such individuals, thus, typically requires significant adjustments in food consumption, and pharmaceutically active agents that increase insulin secretion and/or suppress the appetite of the individual.

Various entities have thus developed pharmaceutically active agents and therapies that treat abnormal insulin secretion. In view of the beneficial metabolic activity induced by GLP-1, the pharmaceutically active agents and associated therapies primarily comprise activation of the GLP-1 receptor proteins on endogenous gastrointestinal (GI) cells.

Such pharmaceutically active agents include semaglutide (Ozempic®, Rybelsus®, Wegovy®), dulaglutide (Trulicity®), exenatide (Bydureon BCise®, Byetta®), and liraglutide (Victoza®, Saxenda®).

The noted pharmaceutically active agents (referred to hereinafter as "GLP-1 analogs") mimic endogenous GLP-1 and are adapted to activate the GLP-1 receptors on endogenous GI cells and, hence, function as GLP-1 receptor agonists.

Although the GLP-1 analogs can effectively activate GLP-1 receptors on pancreatic β-cells and, hence, can induce insulin secretion and suppress the appetite of an individual, there are several drawbacks and disadvantages associated with administration of the GLP-1 analogs to patients.

A major drawback associated with administration of the GLP-1 analogs to patients is the high risk of adverse pathological events. One such adverse pathological event is hypoglycemia (i.e., low blood glucose), which can, and often will, present in patients that are also taking or being administered commonly prescribed antidiabetic agents, such as basal insulin and sulfonylureas.

There is also a high risk of induced production of anti-GLP-1 antibodies and binding of endogenous GLP-1 and the GLP-1 analogs to the anti-GLP-1 antibodies, which can, and often will, induce adverse immune responses.

A further major drawback associated with administration of GLP-1 analogs to individuals are the significant side effects that are often presented by the individuals, including nausea, vomiting, diarrhea, abdominal pain, and constipation.

Since most GLP-1 analogs are administered to patients via a subcutaneous injection, a further drawback associated with GLP-1 analog administration is the pain and discomfort associated with the often-prescribed weekly injections.

Although the GLP-1 analogs developed by Novo Nordisk, which are marketed under the tradename Rybelsus, can also be delivered orally, a significantly greater dose of the Rybelsus GLP-1 analog must be orally administered to an individual to match the pharmacokinetics of the Novo Nordisk injectable GLP-1 analog, which is marketed under the tradename Ozempic, i.e., individuals must be orally administered approximately 100.0 mg/week of the Rybelsus GLP-1 analog to match the efficacy of the typically prescribed 0.5 mg/week of the injectable Ozempic GLP-1 analog.

A further major drawback associated with administration of GLP-1 analogs to individuals is the cost. Indeed, the costs, at present, for a thirty (30) day supply of Ozempic and Rybelsus are approximately $1000.00 and $1200.00, respectively.

As is also well established, in most instances, insulin secretion is also induced by pancreatic β-cells when gastric inhibitory polypeptide (GIP) binds to and activates GIP receptor proteins on the pancreatic β-cells.

Although GIP also induces insulin secretion, there are also several drawbacks and disadvantages associated with administration of GIP alone to patients to treat abnormal insulin secretion.

A major disadvantage is that GIP also induces glucagon secretion from pancreatic (3-cells. Since glucagon is a hyperglycemic compound that increases blood sugar when secreted, the increase in glucagon secretion induced by GIP limits its therapeutic potential for treating abnormal insulin secretion.

To address the above noted disadvantage associated with solely activating the GIP receptor proteins on the pancreatic β-cells, Eli Lilly has recently developed a pharmaceutically active agent that activates GLP-1 and GIP receptors on pancreatic β-cells.

The noted pharmaceutically active agent comprises tirzepatide, i.e., a dual GLP-1/GIP analog marketed under the tradenames Mounjaro® and ZepBound®, which provides the beneficial metabolic activity induced by both GLP-1 and GIP in a synergistic manner without a clinically significant increase in glucagon secretion.

Although the dual GLP-1/GIP analogs can effectively activate both GLP-1 and GIP receptors on GI cells and, hence, can induce insulin secretion, many of the drawbacks and disadvantages associated with administration of the GLP-1 analogs alone to patients are also associated with administration of the dual GLP-1/GIP analogs to patients.

Such drawbacks and disadvantages include the significant side effects that are often presented by the individuals, including nausea, vomiting, diarrhea, abdominal pain, kidney problems, and constipation. Indeed, it has been found that approximately 10% of individuals administered dual GLP-1/GIP analogs suffer from the noted side effects.

A further drawback also associated with dual GLP-1/GIP analog administration to patients is the pain and discomfort associated with the often-prescribed weekly injections. Since there are currently no known dual GLP-1/GIP analogs that are approved by the FDA for oral administration, painful weekly subcutaneous injections are the only available route of administration.

A further major drawback that is similarly associated with administration of dual GLP-1/GIP analogs to individuals is the cost. Indeed, the costs, at present, for a thirty (30) day supply of Mounjaro and Zepbound are similarly approximately $1000.00.

There is thus a need for improved compositions and methods to treat type-2 diabetes mellitus, which substantially reduce or overcome the drawbacks and disadvantages associated with the conventional GLP-1 analogs and dual GLP-1/GIP analogs discussed above.

There is also a need for improved compositions and methods to suppress the appetite of obese individuals with minimal side effects.

It is thus one object of the present invention to provide improved compositions and methods for treating type-2 diabetes mellitus that overcome the drawbacks and disadvantages associated with administration of GLP-1 analogs and dual GLP-1/GIP analogs to patients.

It is another object of the present invention to provide improved compositions and methods that can be painlessly administered to patients that present with type-2 diabetes mellitus, which effectively modulate GI cell activity and, thereby, modulate systemic insulin secretion by the GI cells in an individual.

It is another object of the present invention to provide improved compositions and methods that can be painlessly administered to individuals that present with obesity, which effectively suppress the individual's appetite with minimal side effects.

It is another object of the present invention to provide olfactory compositions that effectively modulate the endocrine system of a subject, which can be administered to the subject via oral, sublingual, inhalation, intranasal, epidural, intracerebral, transdermal, topical, and injection administration means.

It is another object of the present invention to provide olfactory compositions that can effectuate olfactory receptor (OR)-mediated modulation of endogenous GLP-1 in a subject, which can be administered to the subject via oral, sublingual, inhalation, intranasal, epidural, intracerebral, transdermal, topical, and injection administration means.

It is another object of the present invention to provide olfactory compositions that can effectuate olfactory receptor (OR)-mediated modulation of endogenous GIP in a subject, which can be administered to the subject via oral, sublingual, inhalation, intranasal, epidural, intracerebral, transdermal, topical, and injection administration means.

It is another object of the present invention to provide olfactory compositions that can effectively treat adverse endocrine responses and, hence, endocrine diseases and disorders associated therewith without significant side effects.

SUMMARY OF THE INVENTION

The present invention is directed to olfactory compositions and methods for treating endocrine diseases and disorders, and underlying causes thereof.

In some embodiments of the invention, there are thus provided compositions for treating type-2 diabetes mellitus and obesity.

In one embodiment of the invention, the composition (referred to hereinafter as a "GLP-1/PYY secretion composition") comprises a delivery medium (or carrier), 3-methylpentanoic acid, farnesol, eugenol, and nonanoic acid.

In some embodiments, the delivery medium comprises glycerin-based water.

In a preferred embodiment, the $EC_{50}$ value, i.e. concentration sufficient to induce at least 50% activation of an ectopic olfactory receptor, of 3-methylpentanoic acid contained in the GLP-1/PYY secretion composition comprises in the range of approximately 10.0 μM to 30.0 μM.

In a preferred embodiment, the $EC_{50}$ value of farnesol contained in the GLP-1/PYY secretion composition comprises in the range of approximately 0.4 μM to 0.5 μM.

In a preferred embodiment, the $EC_{50}$ value of eugenol contained in the GLP-1/PYY secretion composition comprises in the range of approximately 1.0 μM to 15.0 μM.

In a preferred embodiment, the $EC_{50}$ value of nonanoic acid contained in the GLP-1/PYY secretion composition comprises in the range of approximately 0.1 μM to 0.2 μM.

In a preferred embodiment, the GLP-1/PYY secretion composition activates OR51E1, a seminal ectopic olfactory receptor, in vivo, whereby insulin secretion is induced, and appetite is suppressed.

In some embodiments of the invention, there are also provided methods for treating type-2 diabetes mellitus and obesity comprising the steps of:

(a) providing a GLP-1/PYY secretion composition comprising a delivery medium (or carrier), 3-methylpentanoic acid, farnesol, eugenol, and nonanoic acid; and
(b) delivering the GLP-1/PYY secretion composition to a patient presenting with type-2 diabetes mellitus and obesity, whereby insulin secretion is induced, and appetite is suppressed.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified compounds, compositions or methods, as such may, of course, vary. Thus, although a number of compounds, compositions and methods similar or equivalent to those described herein can be used in the practice of the present invention, the preferred compounds, compositions and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an active agent" includes two or more such agents and the like.

Definitions

The terms "protein", "peptide", "polypeptide" and "polypeptide fragment" as used interchangeably herein, mean, and include amino acid polymers residues of any length. The amino acid polymer can be linear or branched, comprise modified amino acids or amino acid analogs, and it can be interrupted by chemical moieties other than amino acids. The terms "protein", "peptide", "polypeptide" and "polypeptide fragment" also include amino acid polymers that have been modified naturally or synthetically by chemical intervention; by way of example, disulfide bond formation, glycosylation, lipidation, acetylation, phosphorylation, PEGylation or any other manipulation or modification, such as conjugation with a labeling or bioactive component.

The term "endocrine factor" as used herein, means, and includes any molecular compound that is produced and secreted by endogenous cells and induces biological activity at a biological tissue site. The term "endocrine factor" thus means and includes, without limitation, glucagon-like peptide-1 (GLP-1), gastric inhibitory polypeptide (GIP), Peptide Y-Y (PYY), ghrelin, gastrin, cholecystokinin (CCK), bombesin/gastrin releasing peptide (BBS/GRP), neurotensin (NT), glucagon-like peptide 2 (GLP-2), calcitonin gene-related peptide (CGRP), chromogranin A, enteroglucagon, galanin, leptin, motilin, amylin, neuropeptide Y (NPY), pancreatic polypeptide, substance P, oxyntomodulin, and somatostatin.

The term "agonist" as used herein, means, and includes any molecule which binds to a receptor on a cell, wherein the binding to the receptor can potentially lead to subsequent changes in the cell's functions. When an agonist binds to a sufficient number of receptors, the receptors can activate seminal processes in the cell.

The term "antagonist", as used herein, means and includes a molecule, which binds to a receptor on a cell and inhibits the receptor from activating processes in the cell. The inhibition of the receptor can include competitive binding against agonists (when an antagonist is bound, agonists cannot bind to the receptor) and allosteric effects (when the antagonist binds, agonists can still bind the receptor, but cannot activate the receptor).

The term "olfactory receptor (OR)" as used herein, means, and includes an olfactory receptor that is a seminal component of the chemosensory organs responsible for olfaction. The term "olfactory receptor" as used herein, also means, and includes, trace amine associated receptors, vomeronasal receptors, formyl peptide receptors, membrane guanylyl cyclase, subtype GC-D receptors; and G-protein coupled receptors, such as G-protein coupled taste receptors. Olfactory receptors can also include hybrid receptors synthesized from the above-noted olfactory receptors.

The term "ectopic olfactory receptor", as used herein, means, and includes an olfactory receptor that is present in organs, tissue, and/or cells that is a seminal component of physiological processes outside of olfaction and, in some instances, indirectly involved with olfactory-mediated processes.

The term "compound", as used herein, means, and includes any composition of matter comprising two or more chemical elements. According to the invention, in some instances, the terms "compound" and "ligand" are synonymous and used interchangeably herein.

The term "compound" thus means and includes, without limitation, 3-methylpentanoic acid, pentanoic acid, pentanol, 4-methylnonanoic acid, eugenol, farnesol, farnesyl thiosalicylic acid, acrolein, formalin, hydrogen peroxide, coumarin, dicyclohexyl disulfide, nonanoic acid, octanioic acid, 2-nonanoic acid, butyric acid, heptanoic acid, decanoic acid, tetradecanoic acid, trans-2-decenoic acid, tridecanoic acid, undecanoic acid, methyl eugenol, methyl salicylate, (+)-menthol, eugenyl acetate, 2,4-dinitrotoluene, 4-hydroxynonenal, hexanoic acid, 2-ethylhexanoic acid, 2-ethyl-3,5-dimethylpyrazine, pyrazine, dimethyl disulfide, methyl furfuryl disulfide, propanal, butyl butyryl lactate, isovaleric acid, propionic acid, 4-methylpentanoic acid, methanoic acid, octanoic acid, octanal, coumarin, helional, lilial, β-ionone, androstenone, androstadienone, caramel furanone, 3-phenyl propyl propionate, ethyl vanillin, 2-ethyl-fencol, N-amyl acetate, eugenol acetate, sandalwood, S-(−)-citronellol, (−)-citronellol, hydroxycitronellal, citral, S-(−)-citronellal, (+)-carvine, (−) carvone, (+) carvone, linalool, bourgeonal, acetophenone, amyl butyrate, nonanethiol, allyl phenyl acetate, N-amyl acetate, muscone, isoeugenol, eugenol methyl ether, heptanol, hexanol, hexyl acetate, 1-hexanol, 1-heptanol, 2-heptanone, octanol, 1-octanol, celery ketone, anis aldehyde, vanillin, guaiacol, hydroxymethylpentylcyclohexenecarboxaldehyde (lyral), allyl phenylacetate, allyl isothiocyanate, benzyl acetate, 3,4-hexanedione, cis-3-hexen-1-ol, quinoline, ethyl heptanoate, methyl octanoate, nonanal, 1-nonanol, 2-nonanol, 3-octanone, 3-nonanone, decyl aldehyde, (E)-non-2-enal 2-ethyl-3,5-dimethylpyrazine 3-methylbut-2-ene-1-thiol, (2E,6Z)-nona-2,6-dienalcitral, ethyl octanoate, p-mentha-8-thiol-3-one, β-myrcene, γ-decalactone, (S)-(+)-carvone, dihydrojasmone, cinnamaldehyde, spearmint, coffee difuran, quinoline, butyl anthranilate 2,2-dithiodimethylenedifuran, ethyl hexanoate, limonene, α-terpineol, eugenol (3E,5Z)-undeca-1,3,5-triene, long-chain free fatty acids (e.g., palmitic acid and stearic acid), medium-chain free fatty acids (e.g., caproic acid (C6:0), caprylic acid (C8:0), capric acid (C10:0), and lauric acid (C12:0)), and omega-3 polyunsaturated fatty acids (e.g., alpha-linoleic acid, docosahexaenoic acid and eicosatetraenoic acid).

The term "compound" also means and includes any composition of matter included in the Food and Drug Administration's (FDA's) generally recognized as safe (GRAS) database.

The terms "composition", "formulation", "olfactory composition" and "olfactory formulation", as used interchangeably herein, mean, and include any compound or combination of compounds that can interact with and modulate at least one olfactory receptor and/or ectopic olfactory receptor.

The terms "olfaction" and "olfactory reception" as used interchangeably herein, mean, and include the interaction of a composition (or formulation) with an olfactory receptor coupled to a cell signaling pathway. The composition can also be defined as an "odorant" and may be airborne (i.e., volatile) and/or in solution.

The terms "express" and "expression" as used interchangeably herein, mean, and include the production of a protein product from the genetic information contained within a nucleic acid sequence.

The term "upregulation", as used herein, means, and includes the increased production of a protein product from the genetic information contained within a nucleic acid sequence.

The term "downregulation", as used herein, means, and includes the decreased production of a protein product from the genetic information contained within a nucleic acid sequence.

The terms "delivery" and "administration" are used interchangeably herein, and mean and include providing a composition (or formulation), through any method appropriate to deliver the composition (or formulation) to a subject. According to the invention, such administration means includes, without limitation, oral, sublingual, inhalation, intranasal, epidural, intracerebral, transdermal, topical, and injection administration means.

The term "$EC_{50}$", as used herein, means, and includes the concentration of a substance (e.g., a compound or a drug), which, after delivery to a subject, induces at least 50% activation or enhancement of a biological process.

In some embodiments, the term "$EC_{50}$" refers to the concentration of agonist which, after delivery to a subject, induces a response halfway between the baseline and maximum response in an in vitro assay.

In some embodiments, the term "$EC_{50}$" refers to the concentration of a modulator (e.g., an agonist) which, after delivery to a subject, induces at least 50% activation of a receptor type, by way of example, an ectopic olfactory receptor.

The term "$IC_{50}$", as used herein, means, and includes the concentration of a substance (e.g., a compound or a drug), which, after delivery, inhibits or attenuates at least 50% of a biological process.

In some embodiments, the term "$IC_{50}$" refers to the concentration of a modulator (e.g., an antagonist or inhibitor), which, after delivery, inhibits or attenuates at least 50% of receptor activity, e.g., at least 50% of an ectopic olfactory receptor activity.

The term "comprise" and variations of the term, such as "comprising" and "comprises", means "including, but not limited to" and is not intended to exclude, for example, other compounds, ligands or method steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention.

As indicated above, the present invention is directed to compositions and methods for treating diabetes mellitus and obesity by modulating ectopic olfactory activity.

As discussed above, various entities have developed GLP-1 analogs that mimic endogenous GLP-1 alone, and dual GLP-1/GIP analogs that mimic both endogenous GLP-1 and GIP in combination.

As also discussed above, the GLP-1 analogs activate the GLP-1 receptor on pancreatic β-cells and the dual GLP-1/GIP analogs activate both GLP-1 receptor and GIP receptor on pancreatic β-cells to modulate insulin secretion by the pancreas.

Although the GLP-1 analogs and dual GLP-1/GIP analogs can effectively modulate insulin secretion, as also discussed in detail above, there are several drawbacks and disadvantages associated with administration of GLP-1 analogs and dual GLP-1/GIP analogs to patients, including, a high risk of hypoglycemia, adverse side effects, and high costs.

As discussed in detail below, Applicant has developed compositions that directly and effectively modulate production of endogenous GLP-1 and GIP in vivo, which overcome the drawbacks and disadvantages associated with GLP-1 analogs that merely mimic endogenous GLP-1, and dual GLP-1/GIP analogs that merely mimic endogenous GLP-1 and GIP.

Although the compositions of the invention are described in connection with the treatment of endocrine diseases and disorders; more particularly, the treatment of type-2 diabetes mellitus, and underlying causes thereof; specifically, obesity, use of the compositions is not limited solely to the treatment of endocrine diseases and disorders, and underlying causes thereof. As will readily appreciated by one having ordinary skill in the art, the compositions can also be employed to effectively treat additional diseases and/or disorders, including, without limitation, cardiovascular diseases and disorders, reproductive diseases and disorders, immune diseases and disorders, etc.

According to the invention, the compositions of the invention effectuate the following highly effective and, hence, desirable pharmacodynamic activity.

Olfactory Receptor-Mediated GLP-1 and Peptide Y-Y (PYY) Secretion

Figure 1:
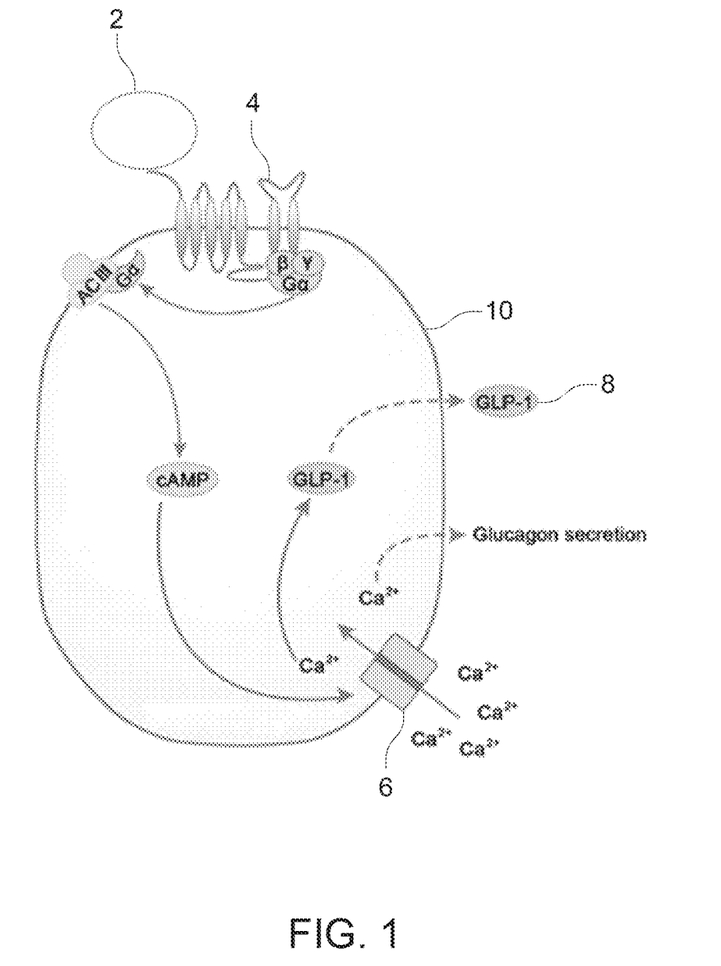
FIG. 1 is a schematic illustration of ectopic olfactory receptor-mediated activation of GLP-1 secretion from endogenous gastrointestinal cells.

Referring to FIG. 1, in a preferred embodiment, the compositions (denoted "2") of the invention target and bind to ectopic olfactory receptors (ORs) (denoted "4") disposed on enteroendocrine cells (in this instance, enteroendocrine L-cells) and pancreatic α-cells (both denoted "10"). The glucose-induced membrane depolarization of the enteroendocrine and α-cells 10 opens the voltage-dependent Ca$^{2+}$ (VDC) channels (denoted "6") of the enteroendocrine and α-cells 10, and the resulting Ca$^{2+}$ influx triggers vesicular exocytosis and increases secretion of GLP-1 (denoted "8") from the cells.

The secreted GLP-1 binds to and activates GLP-1 receptor proteins on pancreatic β-cells, which, as indicated above, induces secretion of insulin.

The secreted insulin then binds to the insulin receptors (IR) of endogenous cells to effectuate the activation of cell signaling cascades that modulate energy metabolism and decrease blood glucose.

The secreted insulin also binds to insulin receptors (IR) of the endogenous hepatic cells to suppress hepatic glucose output by inhibiting adipose lipolysis and, thereby, release of glucose into an individual's bloodstream.

The secreted GLP-1 also binds to and activates GLP-1 receptor proteins on endogenous GI cells, such as islet cells of the pancreas, whereby glucagon release is suppressed. The secreted GLP-1 also suppresses glucagon secretion indirectly via its insulinotropic effect on the pancreatic β-cells, more particularly, the secretion of further suppressors of glucagon secretion by endogenous GI cells, e.g., amylin, zinc, and γ-aminobutyric acid (GABA).

The secreted GLP-1 can also bind to GLP-1 receptor proteins on endogenous brain cells, more specifically, glutamatergic neurons of the hindbrain, which can, and often will, decrease the rate of gastric emptying and acid secretion, and, thereby, reduce appetite.

The binding of GLP-1 to the GLP-1 receptor proteins on endogenous enteroendocrine cells also induces peptide Y-Y (PYY) secretion by the endogenous enteroendocrine cells. PYY then subsequently binds to neuropeptide Y receptors on local central nervous system cells, which activate seminal cell signaling cascades that increase the efficiency of digestion and nutrient absorption after meal consumption to promote satiety and suppress appetite.

The compositions of the invention thus increase insulin secretion and suppress appetite and, hence, provide an effective means of treating diabetes mellitus, and particularly type-2 diabetes mellitus, and obesity.

As discussed in detail below, in preferred embodiment, the compositions of the invention thus comprise at least one compound or ligand that is adapted to bind to and activate an ectopic olfactory receptor, whereby insulin secretion is increased, and appetite is suppressed.

In a preferred embodiment, activation of an ectopic olfactory receptor effectuates increased insulin secretion and appetite suppression by inducing secretion of GLP-1 and/or PYY from endogenous GI cells.

According to the invention, suitable compounds (and ligands) include, without limitation, 3-methylpentanoic acid, pentanoic acid, pentanol, 4-methylnonanoic acid, eugenol, farnesol, farnesyl thiosalicylic acid, acrolein, formalin, hydrogen peroxide, coumarin, dicyclohexyl disulfide, nonanoic acid, octanioic acid, 2-nonanoic acid, butyric acid, heptanoic acid, decanoic acid, tetradecanoic acid, trans-2-decenoic acid, tridecanoic acid, undecanoic acid, methyl eugenol, methyl salicylate, (+)-menthol, eugenyl acetate, 2,4-dinitrotoluene, 4-hydroxynonenal, hexanoic acid, 2-ethylhexanoic acid, 2-ethyl-3,5-dimethylpyrazine, pyrazine, dimethyl disulfide, methyl furfuryl disulfide, propanal, butyl butyryl lactate, isovaleric acid, propionic acid, 4-methylpentanoic acid, methanoic acid, octanoic acid, octanal, coumarin, helional, lilial, β-ionone, androstenone, androstadienone, caramel furanone, 3-phenyl propyl propionate, ethyl vanillin, 2-ethyl-fencol, N-amyl acetate, eugenol acetate, sandalwood, S-(−)-citronellol, (−)-citronellol, hydroxycitronellal, citral, S-(−)-citronellal, (+)-carvine, (−) carvone, (+) carvone, linalool, bourgeonal, acetophenone, amyl butyrate, nonanethiol, allyl phenyl acetate, N-amyl acetate, muscone, isoeugenol, eugenol methyl ether, heptanol, hexanol, hexyl acetate, 1-hexanol, 1-heptanol, 2-heptanone, octanol, 1-octanol, celery ketone, anis aldehyde, vanillin, guaiacol, hydroxymethylpentylcyclohexenecarboxaldehyde (lyral), allyl phenylacetate, allyl isothiocyanate, benzyl acetate, 3,4-hexanedione, cis-3-hexen-1-ol, quinoline, ethyl heptanoate, methyl octanoate, nonanal, 1-nonanol, 2-nonanol, 3-octanone, 3-nonanone, decyl aldehyde, (E)-non-2-enal 2-ethyl-3,5-dimethylpyrazine 3-methylbut-2-ene-1-thiol, (2E,6Z)-nona-2,6-dienalcitral, ethyl octanoate, p-mentha-8-thiol-3-one, β-myrcene, 7-decalactone, (S)-(+)-carvone, dihydrojasmone, cinnamaldehyde, spearmint, coffee difuran, quinoline, butyl anthranilate 2,2-dithiodimethylenedifuran, ethyl hexanoate, limonene, α-terpineol, eugenol (3E,5Z)-undeca-1,3,5-triene, long-chain free fatty acids (e.g., palmitic acid and stearic acid), medium-chain free fatty acids (e.g., caproic acid (C6:0), caprylic acid (C8:0), capric acid (C10:0), and lauric acid (C12:0)), and omega-3 polyunsaturated fatty acids (e.g., alpha-linoleic acid, docosahexaenoic acid and eicosatetraenoic acid).

According to the invention, the compounds and ligands (and, hence, compositions formed therefrom) are adapted to bind to and activate any ectopic olfactory receptor, including, without limitation, adipose olfactory receptors (e.g., OR51E2, OR2W3, OR51E1, OR2A1/42, OR2A4/7, OR52N4, OR13A1, 047D2, OR10J10R1L8, OR2B6, OR4D6, OLFR16, TAS1R3, TAS2R10, TAS2R13, TAS2R14, TAS2R19, TAS2R20, TAS2R31, TAS2R40, TAS2R42, TAS2R5, VN1R1, and VN1R2), adrenal olfactory receptors (e.g., OR51E2, ORW3, OR51E1, OR2A1/42, OR2A4/7, OR52N4, OR13A1, OR5K2, OR3A2, OR2H2, OR7C1, OR2L13, OR1L8, OR2T8, OR10AD1, OR52B6, OR1E1, OR13J1, OR2C1, OR52D1, OR10A2, OR2B6, OR8G5, OR1F12, OR4D6, TAS1R1, TAS1R3, TAS2R10, TAS2R13, TAS2R14, TAS2R19, TAS2R20, TAS2R3, TAS2R30, TAS2R31, TAS2R4, TAS2R42, TAS2R5, TAS2R50, TAS2R9, and VN1R1), central nervous system (CNS) olfactory receptors (e.g., OR51E2, OR2W3, OR4N4, OR51E1, OR52N4, OR13A1, OR5K2, OR7D2, OR3A2, OR2V1, OR2H2, OR7C1, OR2L13, OR1L8, OR2T8, OR10AD1, OR3A3, OR2K2, OR13J1, OR2C1, OR7A5, OR10A2, OR1F12, TAAR3, TAAR5, TAAR6. TAS1R1, TAS1R3, TAS2R1, TAS2R10, TAS2R13, TAS2R14, TAS2R19, TAS2R20, TAS2R3, TAS2R30, TAS2R31, TAS2R39, TAS2R4, TAS2R40, TAS2R42, TAS2R46, TAS2R5, TAS2R50, TAS2R7, TAS2R8, TAS2R9, VN1R1, VN1R2, and VN1R5), dopaminergic neuron olfactory receptors (e.g., OR51E1, OR51E2, and OR2J3), mammary olfactory receptors (e.g., OR51E2, OR51E1, OR2A1/42, OR2A4/7, OR52N4, OR5K2, OR3A2, OR2T8, OR10AD1, OR3A3, OR2K2, OR1E1, OR2C1, OR2C3, OR8D1, OR7A5, OR10A2, TAS1R1, TAS1R3, TAS2R10, TAS2R13, TAS2R14, TAS2R19, TAS2R20, TAS2R31, TAS2R4, TAS2R5, and VN1R1), cardiovascular olfactory receptors (e.g., OR51E2, OR51E1, OR52N4, OR13A1, OR2H2, OR10AD1, OR3A3, OR52B6, OR2K2, OR8G5, OR4D6, TAS1R1, TAS1R3, TAS2R10, TAS2R13, TAS2R14, TAS2R19, TAS2R20, TAS2R3, TAS2R30, TAS2R31, TAS2R4, TAS2R43, TAS2R46, TAS2R5, TAS2R50, TAS2R7, and VN1R1), renal olfactory receptors (e.g., OR51E2, OR51E1, OR2A1/42, OR2A4/7, OR5K2, OR1L8, OR10A2, OR1F12, TAS1R1, TAS1R3, TAS2R1, TAS2R10, TAS2R14, TAS2R19, TAS2R20, TAS2R3, TAS2R30, TAS2R31, TAS2R4, TAS2R42, TAS2R43, TAS2R5, TAS2R50, and VN1R1), hepatic olfactory receptors (e.g., OR2W3, OR51E1, OR2A1/42, OR2A4/7, OR7D2, OR1L8, OR2T8. TAS1R3, TAS2R14, TAS2R14, TAS2R20, TAS2R30, TAS2R30, TAS2R40, TAS2R5, VN1R1, and VN1R2), lymphatic olfactory receptors (e.g., OR51E2, OR51E1, OR2W3, OR2A1/42, OR2A4/7, OR52N4, OR13A1, OR5K2, OR7D2, OR3A2, OR2H2, OR3A3, OR2B6, OR52B6, TAS1R3, TAS2R14, TAS2R19, TAS2R20, TAS2R31, TAS2R4, TAS2R5, TAS2R40, TAS2R50, TAS2R43, TAS2R5 and VN1R1), ovarian olfactory receptors (e.g., OR51E2, OR2W3, OR4N4, OR51E1, OR2A1/42, OR2A4/7, OR52N4, OR5K2, OR3A2, OR2V1, OR2H2, OR2L13, OR1L8, OR10AD1, OR3A3, OR52B6, OR13J1, OR2C1, OR52D1, OR51B5, OR1F12, TAS1R1, TAS1R3, TAS2R1, TAS2R10, TAS2R13, TAS2R14, TAS2R19, TAS2R20, TAS2R3, TAS2R31, TAS2R4, TAS2R42, TAS2R43, TAS2R5, TAS2R50, TAS2R60, TAS2R7, VN1R1, and VN1R2), prostate olfactory receptors (e.g., OR51E2, OR2W3, OR51E1, OR2A1/42, OR2A4/7, OR52N4, OR13A1, OR5K2, OR2H2, OR7C1, OR1E1, OR13J1, OR51B5, TAS1R3, TAS2R14, TAS2R19, TAS2R20, TAS2R43, TAS2R46, TAS2R5, and VN1R1), dermal olfactory receptors (e.g., OR2AT4), testicular olfactory receptors (e.g., OR4N4, OR6F1, OR2H1, OR51E2, OR2W3, OR4N4, OR51E1, OR2A1/42, OR2A4/7, OR52N4, OR7D2, OR3A2, OR2V1, OR2H2, OR7C1, OR10J1, OR1L8, OR1C1, OR2H1, OR10AD1, OR3A3, OR13C3, OR2K2, OR1E1, OR2C1, OR2K2, OR1E1, OR2C1, OR2C3, OR8D1, OR52D1, OR7A5, OR10A2, OR2B6, OR7E24, OR6F1, OR8G5, OR51B5, OR1F12, TAS1R1, TAS1R3, TAS2R1, TAS2R14, TAS2R19, TAS2R20, TAS2R3, TAS2R31, TAS2R4, TAS2R43, TAS2R5, TAS2R50 TAS2R60, VN1R1, VN1R2, VN1R3, and VN1R4), hematologic olfactory receptors (e.g., OR2W3, OR2A4/7, OR52N4, OR7D2, OR2L13, OR3A3, OR2C1, OR2C3, OR2B6, TAS1R3, TAS2R14, TAS2R20, TAS2R40, and TAS2R60), and trace amine-associated receptors (e.g., TAAR1, TAAR2, TAAR3, TAAR4P, TAAR5, TAAR6, TAAR7P, TAAR8, and TAAR9).

Other ectopic olfactory receptors found in other tissues, organs and cells are described in U.S. application Ser. Nos. 15/927,083 and 17/048,059, which are incorporated by reference in their entirety for all purposes described herein.

In some embodiments, the compounds and ligands (and, hence, compositions formed therefrom) of the invention are also adapted to bind to and activate gastrointestinal (GI) olfactory receptors (e.g., OR51E2, OR2W3, OR51E1, OR2A1/42, OR2A4/7, OR2C1, OR5K2, OR7D2, OR7C1, OR2L13, OR7A5, OR51B5, TAS1R1, TAS1R3, TAS2R14, TAS2R20, TAS2R4, TAS2R43, TAS2R5, and VN1R1).

According to the invention, the compounds and ligands (and, hence, compositions formed therefrom) are also preferably adapted to bind to and activate any combination of the aforementioned olfactory receptors.

In a preferred embodiment, the compounds and ligands (and, hence, compositions formed therefrom) of the invention are specifically adapted to bind to and activate at least one olfactory receptor including, without limitation, olfactory receptor family 51 subfamily E member 1 (OR51E1), olfactory receptor family 1 subfamily A member 1 (OR1A1), olfactory receptor family 2 subfamily C member 1 (OR2C1), and olfactory receptor family 10 subfamily J member 5 (OR10J5).

In some embodiments, the compounds and ligands (and, hence, compositions formed therefrom) of the invention comprise at least one of the compounds listed below in Table I below.

TABLE I

| Olfactory Receptor | Expression Site | Compounds/Ligands | Signaling Pathway | Biological Process |
|---|---|---|---|---|
| OR51E1 | Enteroendocrine L-Cell | Nonanoic Acid<br>Butyl Butyryl Lactate<br>Farnesol<br>3-Methylpentanoic Acid<br>4-Methylpentanoic Acid<br>Eugenol<br>Isovaleric Acid | AC3-cAMP | Increased GLP-1 Secretion and Activation |
|  |  | Nonanoic Acid<br>Pentanol<br>Farnesol<br>3-Methylpentanoic Acid<br>4-Methylpentanoic Acid<br>Eugenol<br>Isovaleric Acid | cAMP-Mediated | Increased Peptide Y-Y Secretion and Activation |
| OR1A1 | Enteroendocrine L-Cell | Citronellal<br>Hydroxycitronellal<br>Citral<br>Geraniol | AC3-cAMP |  |
|  |  | 3-Methyl-2,4-Nonanedione<br>Estragole<br>Neroli<br>Heptanol<br>Octanol<br>Helional<br>Nonanal | cAMP-Mediated | Increased GLP-1 Secretion and Activation |
| OR2C1 | Pancreatic β-Cells | Octanoic Acid | PLC-IP$_3$ | Upregulation of Glycerol Kinase Protein |
|  |  | Eugenol<br>Musk Ketone<br>(+)-Dihydrocarvone | cAMP-Mediated | Upregulation of Glycerol Kinase Protein |

TABLE I-continued

| Olfactory Receptor | Expression Site | Compounds/Ligands | Signaling Pathway | Biological Process |
|---|---|---|---|---|
| OR10J5 | Hepatocytes | α-Cedrene Lyral Thujopsene | CAMP-PKA-CREB CAMP-PKA-AMPK | Downregulation of Lipogenesis Genes |

According to the invention, the compositions of the invention that are adapted to activate GLP-1 and/or PYY secretion (referred to hereinafter as "GLP-1/PYY secretion compositions") can comprise any combination of the aforementioned compounds.

OR51E1 Modulation

In a preferred embodiment, the GLP-1/PYY secretion compositions of the invention comprise one or more compounds and/or ligands that are adapted to modulate the activity of OR51E1, more particularly, activate OR51E1 whereby, a conformational change is induced in the molecular structure of OR51E1.

According to the invention, activation of OR51E1 then induces a glucose-induced membrane depolarization of endogenous GI cells, more particularly, L-enteroendocrine and pancreatic α-cells and, thereby, opens the voltage-dependent $Ca^{2+}$ (VDC) channels of the L- and α-cells, and the resulting $Ca^{2+}$ influx triggers vesicular exocytosis and increases secretion of GLP-1.

The secreted GLP-1 binds to and activates GLP-1 receptor proteins on pancreatic β-cells, which, as indicated above, induces secretion of insulin into a subject's blood stream.

The secreted insulin then binds to the insulin receptors (IR) of endogenous cells to effectuate the activation of cell signaling cascades that modulate energy metabolism and decrease blood glucose.

In some embodiments, the GLP-1/PYY secretion compositions of the invention comprise at least one compound or ligand that is adapted to bind to and activate OR51E1 to modulate secretion and/or activation of at least one of the aforementioned additional endocrine factors.

According to the invention, the additional endocrine factors can include, without limitation, ghrelin, gastrin, cholecystokinin (CCK), bombesin/gastrin releasing peptide (BBS/GRP), neurotensin (NT), glucagon-like peptide 2 (GLP-2), calcitonin gene-related peptide (CGRP), chromogranin A, enteroglucagon, galanin, leptin, motilin, amylin, neuropeptide Y (NPY), pancreatic polypeptide, substance P, oxyntomodulin, and somatostatin.

As indicated below, in some embodiments, the GLP-1/PYY secretion compositions of the invention comprise a single compound or ligand, such as farnesol.

In some embodiments, the GLP-1/PYY secretion compositions of the invention comprise a combination of compounds and/or ligands, such as farnesol and eugenol. According to the invention, the compositions of the invention can comprise any suitable combination of the aforementioned compounds including, without limitation, (+)-menthol, 2,4-dinitrotoluene, 2-ethylhexanoic acid, 2-nonanoic acid, 3-methylpentanoic acid, 4-methylnonanoic acid, butyl butyryl lactate, butyric acid, decanoic acid, dimethyl disulfide, eugenol, eugenyl acetate, farnesol, heptanoic acid, hexanoic acid, isovaleric acid, methyl eugenol, methyl furfuryl disulfide, methyl salicylate, nonanoic acid, octanioic acid, pentanoic acid, pentanol, propanal, pyrazine, tetradecanoic acid, trans-2-decenoic acid, tridecanoic acid, and undecanoic acid.

In a preferred embodiment of the invention, the GLP-1/PYY secretion compositions of the invention comprise at least one of the following compounds, which, as indicated above, are adapted to activate OR51E1: (i) 3-methylpentanoic acid, (ii) farnesol, (iii) eugenol, and (iv) nonanoic acid. Each of the noted compounds and the pharmacodynamic activity induced thereby is summarized below.

3-Methylpentanoic Acid

As is well established, 3-methylpentanoic acid is a methyl-branched fatty acid and a derivative compound of pentanoic acid, which carries a methyl group at position 3. 3-methylpentanoic acid is a known plant metabolite, animal metabolite, fungal metabolite, and flavoring agent (which has a cheesy, pungent, sour odor).

Applicant has found that when 3-methylpentanoic acid binds to an olfactory receptor, such as OR51E1, the 3-methylpentanoic acid induces a conformational change in the molecular structure of OR51E1 that induces the binding of OR51E1 to $G_{olf stim}$, thereby, activating cyclic adenosine monophosphate (cAMP), which results in an increase in intracellular cAMP levels.

As shown in FIG. 1, the intracellular cAMP molecules activate the opening of cyclic nucleotide gated channels that allow $Ca^{2+}$ and $Na^+$ to enter an endogenous cell (such as an enteroendocrine cell), which leads to depolarization of the cell and initiation of an action potential. As discussed in detail above, activation of an olfactory receptor, in this instance, OR51E1 induces increased in vivo secretion of GLP-1 and PYY.

The secreted GLP-1 binds to and activates GLP-1 receptor proteins on pancreatic β-cells, which, as indicated above, induces secretion of insulin into a subject's blood stream and the secreted PYY binds to neuropeptide Y receptors on local central nervous system cells, which activates seminal cell signaling cascades that increase the efficiency of digestion and nutrient absorption after meal consumption to promote satiety and suppress appetite.

Farnesol

Farnesol is a 15-carbon organic compound that comprises an acyclic sesquiterpene alcohol typically produced from 5-carbon isoprene compounds in both plants and animals. Farnesol is a compound present in many essential oils, such as citronella, neroli, cyclamen, lemon grass, tuberose, rose, musk, balsam, and tolu, and has a subtle floral odor.

Applicant has found that when farnesol binds to an olfactory receptor, such as OR51E1, the farnesol induces a conformational change in the molecular structure of OR51E1 that is substantially similar to the conformational change induced by 3-methylpentanoic acid and, thus, also induces increased in vivo secretion of GLP-1 and PYY.

Eugenol

Eugenol is an allyl chain-substituted guaiacol and a member of the allylbenzene class of chemical compounds. Eugenol is a colorless to pale yellow, aromatic oily liquid extracted from certain essential oils, more particularly, from the essential oils of clove, nutmeg, cinnamon, basil, and bay leaf, and has a spicy, clove-like odor.

Applicant has found that when eugenol binds to an olfactory receptor, such as OR51E1, the eugenol induces a conformational change in the molecular structure of OR51E1 that is substantially similar to the conformational change induced by 3-methylpentanoic acid and, thus, also induces increased in vivo secretion of GLP-1 and PYY.

Nonanoic Acid

Nonanoic acid is an organic nine (9)-carbon fatty acid compound with structural formula $CH_3(CH_2)_7CO_2H$. Nonanoic acid is a colorless, oily liquid with an unpleasant, pungent odor.

Applicant has found that when nonanoic acid binds to an olfactory receptor, such as OR51E1, the nonanoic acid induces a conformational change in the molecular structure of OR51E1 that is substantially similar to the conformational change induced by 3-methylpentanoic acid and, thus, also induces increased in vivo secretion of GLP-1 and PYY.

As indicated above, the GLP-1/PYY secretion compositions of the invention preferably comprise one or more of the following compounds/ligands, which, as indicated above, are adapted to activate OR51E1: (i) 3-methylpentanoic acid, (ii) farnesol, (iii) eugenol, and (iv) nonanoic acid.

According to the invention, the GLP-1/PYY secretion compositions of the invention can also comprise one or more of the following compounds/ligands, which, as indicated above, are similarly adapted to activate OR51E1: (i) butyl butyryl lactate, (ii) isovaleric acid, and (iii) 4-methylpentanoic acid and, thereby, induce increased in vivo secretion of GLP-1 and PYY.

According to the invention, the $EC_{50}$ value of the noted compounds/ligands contained in a GLP-1/PYY secretion composition of the invention can comprise any $EC_{50}$ value or range between the following $EC_{50}$ values:
(i) approximately 1.0 µM to approximately 25.0 M;
(ii) approximately 10.0 µM to approximately 10.0 M;
(iii) approximately 100.0 µM to approximately 5.0 M; and
(iv) approximately 10.0 µM to approximately 0.5 M.

In one preferred embodiment of the invention, the GLP-1/PYY secretion composition comprises 3-methylpentanoic acid, farnesol, eugenol, and nonanoic acid.

In a preferred embodiment, the $EC_{50}$ value of 3-methylpentanoic acid contained in the GLP-1/PYY secretion composition comprises in the range of approximately 5.0 µM to 50.0 µM, more preferably, in the range of approximately 10.0 µM to 30.0 µM.

In a preferred embodiment, the $EC_{50}$ value of farnesol contained in the GLP-1/PYY secretion composition comprises in the range of approximately 0.1 µM to 0.10 µM, more preferably, in the range of approximately 0.4 µM to 0.5 µM.

In a preferred embodiment, the $EC_{50}$ value of eugenol contained in the GLP-1/PYY secretion composition comprises in the range of approximately 0.5 µM to 20.0 µM, more preferably, in the range of approximately 1.0 µM to 15.0 µM.

In some embodiments, the $EC_{50}$ value of eugenol in a composition of the invention, preferably, a GLP-1/PYY secretion composition, comprises approximately 24.0 millimolar (mM).

In a preferred embodiment, the $EC_{50}$ value of nonanoic acid contained in the GLP-1/PYY secretion composition comprises in the range of approximately 0.05 µM to 0.4 µM, more preferably, in the range of approximately 0.1 µM to 0.2 µM.

OR1A1 Modulation

In some embodiments, the compositions of the invention comprise one or more compounds and/or ligands that are specifically adapted to activate OR1A1 whereby, pharmacodynamic activity similar to that induced via activation of OR51E1 (discussed above) is induced (referred to hereinafter as "OR1A1 modulation compositions").

In some embodiments, the OR1A1 modulation compositions comprise at least one compound or ligand that is adapted to bind to and activate OR1A1 to modulate secretion and/or activation of at least one of the aforementioned additional endocrine factors.

According to the invention, the OR1A1 modulation compositions can comprise one or more of the following compounds/ligands, which are adapted to activate OR1A1: (i) geraniol, (ii) citronellol, (iii) 3-methyl-2,4-nonanedione, (iv) estragole, (v) neroli, (vi) heptanol, (vii) octanol, (viii) helional, (ix) nonanal, (x) hydroxycitronellal, and (xi) citral and, thereby, induce increased in vivo secretion of GLP-1 and, in some instances, PYY.

According to the invention, the $EC_{50}$ value of the above noted compounds/ligands contained in a OR1A1 modulation composition of the invention can similarly comprise any $EC_{50}$ value or range between the following $EC_{50}$ values:
(i) approximately 1.0 µM to approximately 25.0 M;
(ii) approximately 10.0 µM to approximately 10.0 M;
(iii) approximately 100.0 µM to approximately 5.0 M; and
(iv) approximately 10.0 µM to approximately 0.5 M.

In some embodiments, the $EC_{50}$ value of geraniol in a OR1A1 modulation composition of the invention comprises in the range of approximately 10.0 µM to approximately 250.0 µM.

In some embodiments, the $EC_{50}$ value of geraniol in a OR1A1 modulation composition of the invention comprises an $EC_{50}$ value of approximately 100.0 µM.

OR2C1 Modulation

In some embodiments, the compositions of the invention comprise one or more compounds and/or ligands that are specifically adapted to activate OR2C1 whereby, the following pharmacodynamic activity is induced (referred to hereinafter as "OR2C1 modulation compositions").

Activation of OR2C1 induces $Ca^{2+}$ release from the endoplasmic reticulum of pancreatic β-cells through the phospholipase C-inositol triphosphate-dependent (PLC-IP3) pathway and, thereby, an increased concentration of intracellular $Ca^{2+}$. The increase in intracellular $Ca^{2+}$ then activates the CaMKK/CaMKIV pathway, which induces glucokinase (GK) expression, thereby inducing glucose absorption by endogenous cells and glucose-stimulated insulin secretion (GSIS) from pancreatic islet cells.

The secreted insulin then similarly binds to the insulin receptors (IR) of endogenous cells to effectuate the activation of cell signaling cascades that modulate energy metabolism and decrease blood glucose.

In some embodiments, the OR2C1 modulation compositions comprise at least one compound or ligand that is adapted to bind to and activate OR2C1 to modulate secretion and/or activation of at least one of the aforementioned additional endocrine factors.

According to the invention, the OR2C1 modulation compositions can comprise one or more of the following compounds/ligands, which are adapted to activate OR2C1: (i) octanoic acid, (ii) eugenol, (iii) musk ketone, and (iv) (+)-dihydrocarvone.

According to the invention, the $EC_{50}$ value of the above noted compounds/ligands contained in a OR2C1 modulation composition of the invention can similarly comprise any $EC_{50}$ value or range between the following $EC_{50}$ values:
(i) approximately 1.0 µM to approximately 25.0 M;
(ii) approximately 10.0 µM to approximately 10.0 M;

(iii) approximately 100.0 µM to approximately 5.0 M; and
(iv) approximately 10.0 µM to approximately 0.5 M.

OR10J5 Modulation

In some embodiments of the invention, the compositions of the invention comprise one or more compounds and/or ligands that are specifically adapted to activate OR10J5 whereby, the following pharmacodynamic activity is induced (referred to hereinafter as "OR10J5 modulation compositions").

Activation of OR10J5 induces downregulation of the seminal lipogenesis associated gene expression, including the expression of C/EBPα, PPARγ, RXR, LXRα, SREBP-1c, ap2, FAS, SCD1, ACC, and mtGPAT genes, and upregulation of mitochondrial and thermogenic gene expression, including the expression of PGC-1α, PRDM16, UCP1, Cytc, Cox4, and Cidea genes through the cAMP/PKA/HSL pathway.

The above noted downregulation of the seminal lipogenesis associated gene expression and upregulation of mitochondrial and thermogenic gene expression modulates lipid metabolism by inhibiting lipogenesis and, thus, reducing lipid accumulation in hepatic cells.

In some embodiments, the OR10J5 modulation compositions comprise at least one compound or ligand that is adapted to bind to and activate OR10J5 to modulate secretion and/or activation of at least one of the aforementioned additional endocrine factors.

According to the invention, the OR10J5 modulation compositions can comprise one or more of the following compounds/ligands, which are adapted to activate OR10J5: (i) α-cedrene, (ii) hydroxymethylpentylcyclohexenecarboxaldehyde (also referred to as "lyral"), and (iii) thujopsene.

According to the invention, the $EC_{50}$ value of the above noted compounds/ligands contained in a OR10J5 modulation composition of the invention can similarly comprise any $EC_{50}$ value or range between the following $EC_{50}$ values:
(i) approximately 1.0 µM to approximately 25.0 M;
(ii) approximately 10.0 µM to approximately 10.0 M;
(iii) approximately 100.0 µM to approximately 5.0 M; and
(iv) approximately 10.0 µM to approximately 0.5 M.

According to the invention, the compositions of the invention can also effectuate the secretion of gastric inhibitory polypeptide (GIP) (referred to herein as "GIP secretion compositions), which also provides desirable pharmacodynamic activity.

Figure 2:
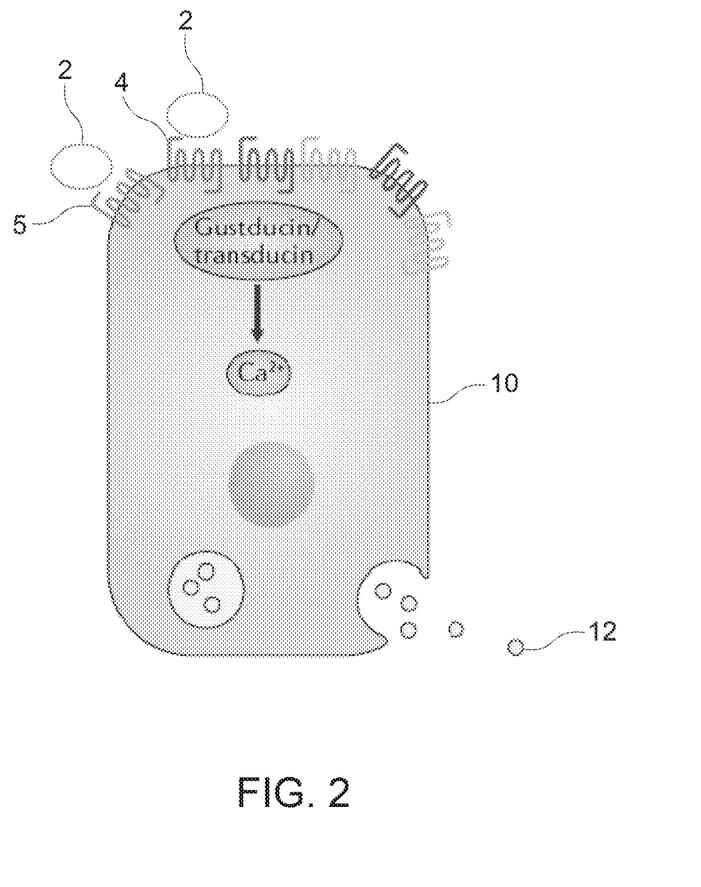
FIG. 2 is a schematic illustration of ectopic olfactory receptor-mediated activation of GIP secretion from endogenous gastrointestinal cells.

Olfactory Receptor-Mediated and Free Fatty Acid Receptor-Mediated (GIP) Secretion Referring now to FIG. 2, in a preferred embodiment, when a GIP secretion composition of the invention (denoted "2") targets and binds to ectopic olfactory receptors (denoted "4") and free fatty acid receptors (denoted "5") disposed on endogenous cells (in this instance, enteroendocrine cells) (denoted "10"), a gustducin-mediated cell signaling pathway is activated, which induces membrane depolarization of the enteroendocrine cells 10 and opens the voltage-dependent $Ca^{2+}$ (VDC) channels of the enteroendocrine cells 10, wherein the resulting $Ca^{2+}$ influx induces vesicular exocytosis and increased secretion (denoted "12") of GIP from the enteroendocrine cells 10.

The secreted GIP binds to and activates GIP receptor proteins on pancreatic β-cells, which, induces secretion of insulin.

The secreted insulin then binds to the insulin receptors (IR) of endogenous cells to effectuate the activation of cell signaling cascades that modulate energy metabolism and decrease blood glucose.

The secreted insulin also binds to insulin receptors (IR) of the endogenous hepatic cells to suppress hepatic glucose output by inhibiting adipose lipolysis and, thereby, release of glucose into an individual's bloodstream.

The secreted GIP also binds to and activates GIP receptor proteins on endogenous GI cells, such as islet cells of the pancreas, to promote pancreatic β-cell survival and prevent apoptosis of pancreatic β-cells by activating the cAMP response element-binding (CREB) and Akt/PKB pathways, thus, directly, and indirectly maintaining a stable population of insulin-producing pancreatic β-cells in vivo.

In a preferred embodiment, the compounds and ligands (and, hence, compositions formed therefrom) of the invention are specifically adapted to bind to and activate at least one olfactory receptor that induces GIP secretion in vivo including, without limitation, olfactory receptor family 2, subfamily W, member 1 (OR2W1), olfactory receptor family 2, subfamily B, member 11 (OR2B11), olfactory receptor family 2 subfamily J member 3 (OR2J3), and transient receptor potential cation channel, subfamily A, member 1 (TRPA1).

According to the invention, the compounds and ligands (and, hence, compositions formed therefrom) of the invention can also be specifically adapted to bind to and activate at least one free fatty acid (FFA) receptor that induces GIP secretion in vivo including, without limitation, free fatty acid receptor 1 (FFAR1) and free fatty acid receptor 4 (FFAR4).

In some embodiments, the compounds and ligands (and, hence, compositions formed therefrom) of the invention comprise at least one of the compounds or ligands listed below in Table II below.

TABLE II

| FFA/Olfactory Receptor | Expression Site | Compounds/Ligands | Signaling Pathway | Biological Process |
|---|---|---|---|---|
| FFAR1 | Enteroendocrine L-Cells | Medium-Chain Free Fatty Acids (e.g., Caproic Acid (C6:0), Caprylic Acid (C8:0), Capric Acid (C10:0), and Lauric Acid (C12:0)) Long-Chain Free Fatty Acids (e.g., Palmitic Acid and Stearic Acid) | Gustducin/ Transducin | Increased GIP Secretion and Activation |
| FFAR4 | Enteroendocrine L-Cells | | | |

TABLE II-continued

| FFA/Olfactory Receptor | Expression Site | Compounds/Ligands | Signaling Pathway | Biological Process |
|---|---|---|---|---|
| | Pancreatic δ-Cells | Omega-3 Polyunsaturated Fatty Acids (e.g., Alpha-Linoleic Acid, Docosahexaenoic Acid, and Eicosatetraenoic Acid) | | Inhibition of Somatostatin to Promote Insulin Secretion |
| OR2W1 | Enteroendocrine L-Cells Adipose Tissue Cells | 2-Heptanone 1-Octanal (−)-Citronellol Hexanal 3-Octanone Hexyl Acetate 1-Hexanol Octanoic Acid 1-Heptanol Allyl Phenylacetate Benzyl Acetate 3,4-Hexanedione Cis-3-Hexen-1-ol | AC3-cAMP | Increased GIP Secretion and Activation |
| OR2B11 | Enteroendocrine L-Cells | 2-Ethyl-3,5-Dimethylpyrazine Coumarin Dicyclohexyl Disulfide Spearmint Coffee Difuran Quinoline Cinnamaldehyde | AC3-cAMP | Increased GIP Secretion and Activation |
| OR2J3 | Enteroendocrine L-Cells | Cis-3-Hexen-1-ol Cinnamaldehyde | AC3-cAMP | Increased GIP Secretion and Activation |
| TRPA1 | Enterochromaffin Cells | Allyl Isothiocyanate Cinnamaldehyde Farnesyl Thiosalicylic Acid Formalin Hydrogen Peroxide 4-Hydroxynonenal Acrolein | $Ca^{2+}$ | Increased GIP Secretion and Activation |

In some embodiments of the invention, the GIP secretion compositions of the invention comprise one or more compounds and/or ligands that are set forth in Table II above, which are specifically adapted to activate FFAR1 (and FFAR4).

According to the invention, the activation of FFAR1 (and FFAR4) by the compounds/ligands induces activation of a gustducin-mediated cell signaling pathway, which induces membrane depolarization of enteroendocrine cells and opens voltage-dependent $Ca^{2+}$ (VDC) channels of the enteroendocrine cells, wherein the resulting $Ca^{2+}$ influx induces increased secretion of GIP from the enteroendocrine cells.

The activation of FFA receptors, such as FFAR1 (and FFAR4), can, in some instances, also induce activation of $G_{aq/11}$ and β-arrestin signaling pathways and, thereby, stimulate further GIP secretion.

The secreted GIP binds to and activates GIP receptor proteins on pancreatic β-cells, which induces secretion of insulin.

The secreted insulin then binds to the insulin receptors (IR) of endogenous cells to effectuate the activation of cell signaling cascades that modulate energy metabolism and decrease blood glucose.

The secreted insulin also binds to insulin receptors (IR) of the endogenous hepatic cells to suppress hepatic glucose output by inhibiting adipose lipolysis and, thereby, release of glucose into an individual's bloodstream.

The secreted GIP also binds to and activates GIP receptor proteins on endogenous GI cells, such as islet cells of the pancreas, to promote pancreatic β-cell survival and prevent apoptosis of pancreatic β-cells by activating the cAMP response element-binding (CREB) and Akt/PKB pathways, thus, directly and indirectly maintaining a stable population of insulin-producing pancreatic β-cells in vivo.

In some embodiments, the GIP secretion compositions comprise at least one compound or ligand that is adapted to bind to and activate FFAR1 (and/or FFAR4) to modulate secretion and/or activation of at least one of the aforementioned additional endocrine factors.

As indicated above, in some embodiments of the invention, the GIP secretion compositions of the invention preferably comprise one or more of the following compounds/ligands, which, as indicated above, are adapted to activate FFAR1 (and/or FFAR4): (i) a medium-chain free fatty acid, (ii) a long-chain free fatty acid, and (iii) an omega-3 polyunsaturated fatty acid (e.g., alpha-linoleic acid, docosahexaenoic acid, and eicosatetraenoic acid).

Medium-Chain Free Fatty Acids

As is well established, a medium-chain free fatty acid is a fatty acid comprising a carboxylic acid head group with a 6-12 carbon aliphatic chain (saturated or unsaturated) with a methyl group on the end of the aliphatic chain. Foods that are rich in medium chain fatty acids include, without limitation, palm kernel oil and coconut oil.

Applicant has found that when a medium-chain free fatty acid binds to a free fatty acid (FFA) receptor, such as FFAR1 or FFAR4, the medium-chain free fatty acid induces a conformational change in the molecular structure of the FFA receptor that induces the intracellular $G_\alpha/G_\beta/G_\gamma$ subunits of the FFA receptor to act as a guanine nucleotide exchange factor and, thus, exchange a guanine diphosphate (GDP) for a guanine triphosphate (GTP), which binds to the Gα subunit of the FFAR1 or FFAR4. The noted binding of the GTP to the $G_\alpha$ subunit then induces a dissociation of the $G_\alpha/G_\beta/G_\gamma$ subunits of the FFAR1 or FFAR4 into a (i) free Gα subunit and a (ii) $G_\beta/G_\gamma$ complex and, thereby, activates seminal downstream cell signaling processes that induce an increase in intracellular cAMP in endogenous cells, such as enteroendocrine cells.

As depicted in FIG. 2, by virtue of the intracellular cAMP level increase, the opening of cyclic nucleotide gated $Ca^{2+}$ channels is induced, which results in increased cellular $Ca^{2+}$ and, thereby, induction of increased secretion of GIP from the endogenous cells.

The secreted GIP binds to and activates GIP receptor proteins on pancreatic β-cells, which, as indicated above, (i) induces secretion of insulin, (ii) promotes pancreatic β-cell survival, and (iii) prevents apoptosis of pancreatic β-cells by activating the cAMP response element-binding (CREB) and Akt/PKB pathways, thus, directly, and indirectly maintaining a stable population of insulin-producing pancreatic β-cells in vivo.

Long-Chain Free Fatty Acids

As is well established, a long-chain free fatty acid is a fatty acid comprising a carboxylic acid head group attached to a 12-21 aliphatic carbon chain that can be saturated or unsaturated and includes a methyl group on the terminal carbon.

Applicant has found that when a long-chain free fatty acid binds to an FFA receptor, such as FFAR1 or FFAR4, the long-chain free fatty acid induces a conformational change in the molecular structure of the FFA receptor that is substantially similar to the conformational change in the molecular structure of an FFA receptor that is induced by a medium-chain free fatty acid and, thus, also induces increased in vivo secretion of GIP.

Omega-3 Polyunsaturated Fatty Acids

As is well established, an omega-3 polyunsaturated fatty acid is a polyunsaturated fatty acid that comprises a carboxylic acid head group attached to a polyunsaturated aliphatic carbon chain with carbon-carbon double bonds disposed three carbons from the terminal methyl group. It is well established that several omega-3-fatty acids are essential dietary molecules, which means that the human body either has difficulty making these molecules or cannot make these molecules and, thus, must be supplied in human diets from outside sources.

Applicant has found that when an omega-3 polyunsaturated fatty acid binds to an FFA receptor, such as FFAR1 or FFAR4, the omega-3 polyunsaturated fatty acid fatty acid induces a conformational change in the molecular structure of the FFA receptor that is substantially similar to the conformational change in the molecular structure of an FFA receptor that is induced by a medium-chain free fatty acid and, thus, also induces increased in vivo secretion of GIP.

According to the invention, the $EC_{50}$ value of the above noted compounds/ligands contained in a GIP secretion composition of the invention can similarly comprise any $EC_{50}$ value or range between the following $EC_{50}$ values:
(i) approximately 1.0 μM to approximately 25.0 M;
(ii) approximately 10.0 μM to approximately 10.0 M;
(iii) approximately 100.0 μM to approximately 5.0 M; and
(iv) approximately 10.0 μM to approximately 0.5 M.

OR2W1 Modulation

In a preferred embodiment, the GIP secretion compositions of the invention comprise one or more compounds and/or ligands that are adapted to modulate the activity of OR2W1, more particularly, activate OR2W1 whereby, a conformational change is induced in the molecular structure of OR2W1.

Applicant has found that when a compound/ligand, e.g., 2-heptanone, binds to OR2W1, the compound induces a conformational change in the molecular structure of the OR2W1 that similarly induces the intracellular $G_\alpha/G_\beta/G_\gamma$ subunits of the olfactory receptor to act as a guanine nucleotide exchange factor and, thus, exchange a guanine diphosphate (GDP) for a guanine triphosphate (GTP), which binds to the $G_\alpha$ subunit of the OR2W1. The noted binding of the GTP to the $G_\alpha$ subunit then induces a dissociation of the $G_\alpha/G_\beta/G_\gamma$ subunits of the OR2W1 into a (i) free $G_\alpha$ subunit and a (ii) $G_\beta/G_\gamma$ complex and, thereby, activates seminal downstream cell signaling processes that induce an increase in intracellular cAMP in endogenous cells, such as enteroendocrine cells.

As depicted in FIG. 2, by virtue of the intracellular cAMP level increase, the opening of cyclic nucleotide gated $Ca^{2+}$ channels is induced, which results in increased cellular $Ca^{2+}$ and, thereby, increased induction of secretion of GIP from the endogenous cells.

The secreted similarly GIP binds to and activates GIP receptor proteins on pancreatic γ-cells, which, as indicated above, (i) induces secretion of insulin, (ii) promotes pancreatic β-cell survival, and (iii) prevents apoptosis of pancreatic β-cells by activating the cAMP response element-binding (CREB) and Akt/PKB pathways, thus, directly and indirectly maintaining a stable population of insulin-producing pancreatic β-cells in vivo.

In some embodiments, the OR2W1 modulation compositions comprise at least one compound or ligand that is adapted to bind to and activate OR2W1 to modulate secretion and/or activation of at least one of the aforementioned additional endocrine factors.

According to the invention, the OR2W1 modulation compositions can comprise one or more of the following compounds/ligands, which are adapted to activate OR2W1: (i) 2-heptanone, (ii) 1-octanal, (iii) (−)-citronellol, (iv) hexanal, (v) 3-octanone, (vi) hexyl acetate, (vii) 1-hexanol, (viii) octanoic acid, (ix) 1-heptanol, (x) allyl phenylacetate, (xi) benzyl acetate, (xii) 3,4-hexanedione, and (xiii) cis-3-hexen-1-ol and, thereby, induce increased in vivo secretion of GIP.

According to the invention, the $EC_{50}$ value of the above noted compounds/ligands contained in a OR2W1 modulation composition of the invention can similarly comprise any $EC_{50}$ value or range between the following $EC_{50}$ values:
(i) approximately 1.0 μM to approximately 25.0 M;
(ii) approximately 10.0 μM to approximately 10.0 M;
(iii) approximately 100.0 μM to approximately 5.0 M; and
(iv) approximately 10.0 μM to approximately 0.5 M.

OR2B11 Modulation

In some embodiments, the compositions of the invention comprise one or more compounds and/or ligands that are specifically adapted to activate OR2B11 whereby, pharmacodynamic activity similar to that induced via activation of OR2W1 (discussed above) is induced (referred to hereinafter as "OR2B11 modulation compositions").

In some embodiments, the OR2B11 modulation compositions comprise at least one compound or ligand that is adapted to bind to and activate OR2B11 to modulate secretion and/or activation of at least one of the aforementioned additional endocrine factors.

According to the invention, the OR2B11 modulation compositions can comprise one or more of the following compounds/ligands, which are adapted to activate OR2B11: (i) 2-ethyl-3,5-dimethylpyrazine, (ii) coumarin, (iii) dicyclohexyl disulfide, (iv) spearmint, (v) coffee difuran, (vi) quinoline, and (vii) cinnamaldehyde and, thereby, induce increased in vivo secretion of GIP.

According to the invention, the $EC_{50}$ value of the above noted compounds/ligands contained in a OR2B11 modulation composition of the invention can similarly comprise any $EC_{50}$ value or range between the following $EC_{50}$ values:
 (i) approximately 1.0 µM to approximately 25.0 M;
 (ii) approximately 10.0 µM to approximately 10.0 M;
 (iii) approximately 100.0 µM to approximately 5.0 M; and
 (iv) approximately 10.0 µM to approximately 0.5 M.

OR2J3 Modulation

In some embodiments, the compositions of the invention comprise one or more compounds and/or ligands that are specifically adapted to activate OR2J3 whereby, pharmacodynamic activity similar to that induced via activation of OR2W1 (discussed above) is induced (referred to hereinafter as "OR2J3 modulation compositions").

In some embodiments, the OR2J3 modulation compositions comprise at least one compound or ligand that is adapted to bind to and activate OR2J3 to modulate secretion and/or activation of at least one of the aforementioned additional endocrine factors.

According to the invention, the OR2J3 modulation compositions can comprise one or more of the following compounds/ligands, which are adapted to activate OR2J3: (i) cis-3-hexen-1-ol and (ii) cinnamaldehyde and, thereby, induce increased in vivo secretion of GIP.

According to the invention, the $EC_{50}$ value of the above noted compounds/ligands contained in a OR2J3 modulation composition of the invention can similarly comprise any $EC_{50}$ value or range between the following $EC_{50}$ values:
 (i) approximately 1.0 µM to approximately 25.0 M;
 (ii) approximately 10.0 µM to approximately 10.0 M;
 (iii) approximately 100.0 µM to approximately 5.0 M; and
 (iv) approximately 10.0 µM to approximately 0.5 M.

TRPA1 Modulation

In some embodiments, the compositions of the invention comprise one or more compounds and/or ligands that are specifically adapted to activate TRPA1 whereby, pharmacodynamic activity similar to that induced via activation of OR2W1 (discussed above) is induced (referred to hereinafter as "TRPA1 modulation compositions").

In some embodiments, the TRPA1 modulation compositions comprise at least one compound or ligand that is adapted to bind to and activate TRPA1 to modulate secretion and/or activation of at least one of the aforementioned additional endocrine factors.

According to the invention, the TRPA1 modulation compositions can comprise one or more of the following compounds/ligands, which are adapted to activate TRPA1: (i) allyl isothiocyanate, (ii) cinnamaldehyde, (iii) farnesyl thiosalicylic acid, (iv) formalin, (v) hydrogen peroxide, (vi) 4-hydroxynonenal, and (vii) acrolein and, thereby, induce increased in vivo secretion of GIP.

According to the invention, the $EC_{50}$ value of the above noted compounds/ligands contained in a TRPA1 modulation composition of the invention can similarly comprise any $EC_{50}$ value or range between the following $EC_{50}$ values:
 (i) approximately 1.0 µM to approximately 25.0 M;
 (ii) approximately 10.0 µM to approximately 10.0 M;
 (iii) approximately 100.0 µM to approximately 5.0 M; and
 (iv) approximately 10.0 µM to approximately 0.5 M.

Preferably, the compositions of the invention are formulated and adapted to activate a plurality of olfactory receptors, e.g., OR51E1, OR2C1, and OR2W1, and a plurality of free fatty acid receptors, e.g., FFAR1 and FFAR4.

Concomitant Modulation of GLP-1 and GIP Secretion

In some embodiments, the compositions of the invention are formulated and adapted to activate OR51E1 and FFAR1, and, thereby, induce concomitant GLP-1 and GIP secretion (referred to herein as "GLP-1/GIP secretion compositions").

According to the invention, GLP-1/GIP secretion compositions can comprise one or more of the compounds/ligands set forth in Tables I and II and discussed above.

In some embodiments, the GLP-1/GIP secretion composition comprises farnesol and at least one omega-3 polyunsaturated fatty acid, such as docosahexaenoic acid.

According to the invention, the $EC_{50}$ value of the compounds/ligands contained in a GLP-1/GIP secretion composition of the invention can similarly comprise any $EC_{50}$ value or range between the following $EC_{50}$ values:
 (i) approximately 1.0 µM to approximately 25.0 M;
 (ii) approximately 10.0 µM to approximately 10.0 M;
 (iii) approximately 100.0 µM to approximately 5.0 M; and
 (iv) approximately 10.0 µM to approximately 0.5 M.

In some embodiments, modulating the activity of multiple olfactory receptors and/or free fatty acid receptors, as described herein, results in elevated endocrine factor levels.

In some embodiments, modulating the activity of multiple olfactory receptors and/or free fatty acid receptors, as described herein, results in synergistically elevated endocrine factor levels.

In some embodiments, modulating the activity of multiple olfactory receptors and/or free fatty acid receptors, as described herein, results in elevated endocrine factor secretion.

In some embodiments, modulating the activity of multiple olfactory receptors and/or free fatty acid receptors, as described herein, results in synergistically elevated endocrine factor secretion.

In some embodiments, modulating the activity of multiple olfactory receptors and/or free fatty acid receptors, as described herein, results in endocrine factor secretion higher than endocrine factor secretion induced when modulating the activity of any single olfactory receptor and/or free fatty acid receptor alone.

In some embodiments, modulating the activity of multiple olfactory receptors and/or free fatty acid receptors, as described herein, induces a beneficial biological response, including, by way of example, increased insulin secretion, lower food consumption, increased body mass reduction, increased cAMP levels, increased nutrient absorption, increased small intestinal length, increased small intestinal weight, increased villus height, or increased villus height/crypt depth ratio than when modulating the activity of any single olfactory receptor and/or free fatty acid receptor alone.

In some embodiments, the compositions of the invention further comprise a physiologically suitable (or acceptable) carrier (also referred to herein as a physiologically suitable (or acceptable) excipient, or physiologically suitable (or acceptable) excipient selected based on a chosen route of administration, e.g., oral administration, and standard pharmaceutical practice.

According to the invention, suitable aqueous and non-aqueous carriers that can be employed in the compositions of the invention include water, ethanol, polyols (such as glycerol, glycerin-based water, propylene glycol, polyethylene glycol, and the like), and suitable mixtures thereof;

vegetable oils, such as olive oil; buffers, such as neutral buffered saline, phosphate buffered saline and the like; carbohydrates, such as glucose, mannose, sucrose and dextrans, mannitol; proteins; polypeptides, and amino acids, such as glycine; antioxidants; chelating agents such as ethylenediaminetetraacetic acid (EDTA) or glutathione; adjuvants (e.g., aluminum hydroxide); and injectable organic esters, such as ethyl oleate and cyclodextrins.

According to the invention, the compositions can be manufactured by means of conventional mixing, dissolving, granulating, dragee-making, levigating, emulsifying, encapsulating, entrapping, and lyophilizing processes. The manufactured compositions can take the form of solutions, suspensions, emulsion, tablets, pills, pellets, capsules, capsules containing liquids, powders, sustained-release formulations, suppositories, emulsions, aerosols, sprays, suspensions, and other forms suitable for administration to a patient.

In some embodiments, proper fluidity of a composition is maintained via coating materials, such as lecithin.

According to the invention, the compositions of the invention can be formulated into any known form suitable for parenteral administration, e.g., injection or infusion. Alternatively, the compositions can be formulated for oral administration, nasal or other mucosal tissue administration, or administration as a suppository (e.g., for small molecules). The compositions can also comprise formulation additives, such as suspending agents, preservatives, stabilizers and/or dispersants, and preservation agents.

According to the invention, the compositions can thus be administered to a patient via any suitable method, including, without limitation, oral, sublingual, inhalation, intranasal, epidural, intracerebral, transdermal, topical, and injection administration means.

The compositions of the invention can also be administered to a patient via intraarterial, subcutaneous, intradermal, intratumoral, intranodal, intramedular, intramuscular, intranasally, and intraperitoneal means.

According to the invention, the compositions of the invention can also be incorporated into various ingestible fluids, such as flavored waters and coffee.

According to the invention, the compositions of the invention can also be incorporated into a food item, such as a cracker, and/or a nutritional supplement or supplemental food item, such as protein bar.

In some embodiments, the compositions of the invention are administered at a dosage of from about 10.0 g/kg to about 50.0 mg/kg, from about 100.0 μg/kg to about 50.0 mg/kg, from about 1.0 mg/kg to about 50.0 mg/kg, and in certain embodiments, from about 5.0 mg/kg to about 25.0 mg/kg, including all integer values within those ranges.

In some embodiments, the compositions are administered at a dose over time from about 1.0 mg to about 5.0 g per day, from about 10.0 mg to about 4.0 g per day, and in certain embodiments, from about 20.0 mg to about 2.0 g per day, including all integer values within those ranges. According to the invention, compositions can also be administered multiple times per day at these dosages.

In at least one embodiment of the invention, there is thus provided a composition for treating an endocrine disease of a patient; particularly, type-2 diabetes, comprising a GLP-1/PYY secretion composition comprising a delivery medium, 3-methylpentanoic acid, farnesol, eugenol, and nonanoic acid, the 3-methylpentanoic acid comprising an $EC_{50}$ value in the range of approximately 5.0 μM to 50.0 μM, more preferably, in the range of approximately 10.0 μM to 30.0 μM, the farnesol comprising an $EC_{50}$ value in the range of approximately 0.1 μM to 0.10 μM, more preferably, in the range of approximately 0.4 μM to 0.5 μM, the eugenol comprising an $EC_{50}$ value in the range of approximately 0.5 μM to 20.0 μM, more preferably, in the range of approximately 1.0 μM to 15.0 μM, and the nonanoic acid comprising an $EC_{50}$ value in the range of approximately 0.05 μM to 0.4 μM, more preferably, in the range of approximately 0.1 μM to 0.2 μM, the GLP-1/PYY secretion composition adapted to induce glucagon-like peptide-1 (GLP-1) and peptide Y-Y (PYY) secretion in vivo, whereby, when the GLP-1/PYY secretion composition is delivered to the patient, insulin secretion of the patient is induced.

In a preferred embodiment, the GLP-1/PYY secretion composition is sufficient to induce at least 50% activation of ectopic olfactory receptor OR51E1 in vivo when delivered to a patient.

As indicated above, the GLP-1/PYY secretion composition can be administered to a patient via any suitable means, including, without limitation, oral, sublingual, inhalation, intranasal, epidural, intracerebral, transdermal, topical, and injection means.

In some embodiments of the invention, there is thus also provided a method of treating an endocrine disorder of a patient comprising the steps of (i) providing one or more of the compositions of the invention described above and (ii) delivering the composition(s) to the subject.

In a least one embodiment, there is thus provided a method of modulating insulin secretion of a patient and, hence, treating type-2 diabetes, comprising the steps of:

(a) providing a composition for treating an endocrine disease; particularly, type-2 diabetes, comprising a GLP-1/PYY secretion composition comprising a delivery medium, 3-methylpentanoic acid, farnesol, eugenol, and nonanoic acid, the 3-methylpentanoic acid comprising an $EC_{50}$ value in the range of approximately 5.0 μM to 50.0 μM, more preferably, in the range of approximately 10.0 μM to 30.0 μM, the farnesol comprising an $EC_{50}$ value in the range of approximately 0.1 μM to 0.10 μM, more preferably, in the range of approximately 0.4 μM to 0.5 μM, the eugenol comprising an $EC_{50}$ value in the range of approximately 0.5 μM to 20.0 μM, more preferably, in the range of approximately 1.0 μM to 15.0 μM, and the nonanoic acid comprising an $EC_{50}$ value in the range of approximately 0.05 μM to 0.4 μM, more preferably, in the range of approximately 0.1 μM to 0.2 μM; and (b) delivering an effective dose of the GLP-1/PYY secretion composition to the patient, wherein the GLP-1/PYY secretion composition induces glucagon-like peptide-1 (GLP-1) and peptide Y-Y (PYY) secretion in vivo, whereby, insulin secretion of the patient is induced.

In a preferred embodiment, the GLP-1/PYY secretion composition is similarly sufficient to induce at least 50% activation of ectopic olfactory receptor OR51E1 in vivo when delivered to the patient.

In some embodiments of the invention, there is also provided a method of treating obesity of a subject comprising the steps of (i) providing one or more of the compositions of the invention described above and (ii) delivering the composition(s) to the subject.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A composition for treating an endocrine disease of a patient, comprising:
   a GLP-1/PYY secretion composition comprising a delivery medium, 3-methylpentanoic acid and farnesol, said 3-methylpentanoic acid comprising an $EC_{50}$ value in said GLP-1/PYY secretion composition in the range of from about 10.0 μM to about 30.0 μM, said farnesol comprising an $EC_{50}$ value in said GLP-1/PYY secretion composition in the range of from about 0.4 μM to about 0.5 μM,
   said GLP-1/PYY secretion composition adapted to induce glucagon-like peptide-1 (GLP-1) and peptide Y-Y (PYY) secretion and, thereby, increased insulin secretion in vivo, when said GLP-1/PYY secretion composition is delivered to said patient.

2. The composition of claim 1, wherein said GLP-1/PYY secretion composition induces at least 50% activation of ectopic olfactory receptor family 51 subfamily E member 1 (OR51E1) in vivo when said GLP-1/PYY secretion composition is said delivered to said patient.

3. The composition of claim 1, wherein said GLP-1/PYY secretion composition further comprises eugenol.

4. The composition of claim 3, wherein said eugenol comprises an $EC_{50}$ value in said GLP-1/PYY secretion composition in the range of from about 1.0 μM to about 15.0 μM.

5. The composition of claim 1, wherein said delivery medium comprises glycerin-based water.

6. The composition of claim 1, wherein said delivery medium comprises ingestible matter.

7. The composition of claim 6, wherein said ingestible matter is selected from the group consisting of an item of food and a beverage.

8. The composition of claim 1, wherein said endocrine disease comprises type-2 diabetes mellitus.

* * * * *